United States Patent [19]

Kwan

[11] Patent Number: 4,496,537
[45] Date of Patent: Jan. 29, 1985

[54] BIOLOGICALLY STABLE ALPHA-INTERFERON FORMULATIONS

[75] Inventor: Henry K. Kwan, Summit, N.J.

[73] Assignee: Schering Corporation, Madison, N.J.

[21] Appl. No.: 532,886

[22] Filed: Sep. 16, 1983

Related U.S. Application Data

[63] Continuation-in-part of Ser. No. 466,707, Feb. 15, 1983, abandoned, which is a continuation-in-part of Ser. No. 334,052, Dec. 23, 1981, abandoned.

[30] Foreign Application Priority Data

Nov. 19, 1982 [ZA] South Africa ............ 82/8580
Dec. 15, 1982 [EP] European Pat. Off. ........ 82111665.4

[51] Int. Cl.$^3$ ................ A61K 45/02; C12P 21/00
[52] U.S. Cl. ................ 424/85; 260/112 R; 435/68
[58] Field of Search ........ 424/85; 260/112 R; 435/68, 811

[56] References Cited

U.S. PATENT DOCUMENTS

| | | | |
|---|---|---|---|
| 2,553,497 | 5/1951 | Orut et al. | 424/92 |
| 2,806,815 | 9/1957 | Singher et al. | 424/92 |
| 3,016,398 | 1/1962 | Larson et al. | 424/92 |
| 4,198,479 | 4/1980 | Tytell et al. | 435/2 |
| 4,289,690 | 9/1981 | Pestka et al. | 424/85 |
| 4,337,242 | 6/1982 | Markus et al. | 424/89 |

FOREIGN PATENT DOCUMENTS 95795 7/1979 Japan.
102519 8/1980 Japan.
866423 4/1961 United Kingdom.
900115 7/1962 United Kingdom.

OTHER PUBLICATIONS

Billiau, A., et al., Antimicrobial Agent and Chemotherapy, vol. 16, pp. 49–55, 1979.

Sedmak, J., et al., "Procedures for Stabilisation of Interferon", in Methods in Enzymology, vol. 78, Part A, Academic Press, pp. 591–595, 1981.

Cantell, K., et al., Proc. of Tissue Culture Association Workshop, Lake Placid, N.Y., pp. 35–39, 1973.

*Primary Examiner*—Blondel Hazel
*Attorney, Agent, or Firm*—Stephen I. Miller

[57] ABSTRACT

The addition of glycine or alanine prior to lyophilization significantly improves the biological stability of alpha type interferon formulations.

7 Claims, No Drawings

BIOLOGICALLY STABLE ALPHA-INTERFERON FORMULATIONS

This application is a continuation-in-part of copending application Ser. No. 466,707 filed on Feb. 15, 1983, now abandoned, which in turn is a continuation-in-part of application Ser. No. 334,052 filed on Dec. 23, 1981, now abandoned.

The present invention relates to lyophilized alpha type interferon formulations which substantially retain their biological activity upon storage. It is widely believed that alpha type interferons have great potential as drugs for the treatment of a wide variety of disease states and particularly for various types of viral infections. The formulations of the present invention are useful in preparing solutions for injection, nasal sprays, nasal solutions, ophthalmic solutions or ointments where an alpha type interferon is the active drug.

In order to avoid possible side effects and to insure reproducibility of observed therapeutic effects, it is desirable to use alpha type interferons of high specific activity. However, the well known biological instability of solutions of alpha type interferons possessing high specific activity makes it difficult to provide biologically stable fromulations for clinical use.

It has been proposed that interferon be packaged in lyophilized form for reconstitution with water. Such a formulation may contain albumin as a stabilizer. Even with albumin however, formulations containing interferon of high specific activity have only limited biological stability.

I have surprisingly found that the addition of glycine or alanine to alpha type interferon solutions, prior to lyophilization, provides a pharmaceutically acceptable lyophilized product that has significantly improved biological stability. The use of glycine (also known as aminoacetic acid) or alanine (also known as $\alpha$-alanine) additionally improves the ability of the lyophilized formulation to be readily reconstituted and it allows freeze drying at a higher temperature than would otherwise be required.

As used herein, the term "alpha type interferon" means an interferon exhibiting biological properties similar to those of human leucocyte interferon. It should be noted that a number of alpha interferon species are known, usually designated by a numeral after the Greek letter. Also included within the scope of this invention are the so-called alpha hybrid interferons wherein fragments of two or more native alpha interferon species are joined (See for instance, EP No. 51873) and the chemically modified alpha-interferons, e.g. point mutations. Preferred forms of alpha type interferon for use in the formulations of the present invention are alpha-1 and alpha-2 interferon. Particularly preferred for use in the formulations of the present invention is alpha-2 interferon which may be prepared by recombinant-DNA methods, for example, those disclosed by Nagata et al., Nature, Vol. 284, pages 316–320 (1980).

Also, in the context of this invention, the term "biologically stable" means that the biological activity of the interferon formulation, as measured in the standard method by inhibition of the cytopathic effect (CPE) of a virus, is substantially retained upon storage for at least six months at 20° C.

In addition to either glycine or alanine and alpha-interferon, the compositions of the present invention also contain a compatible buffer system to maintain a pH in the reconstituted solution of 6.5 to 8.0, preferably about 7.0 to 7.4. A preferred buffer system is a combination of sodium dibasic phosphate and sodium monobasic phosphate.

In the preferred embodiment, glycine is employed as the stabilizer.

The amount of glycine or alanine that should be used in the subject formulations is about 5 to 150 milligrams per milliliter of reconstituted solution. A more preferred range is 5 to 25 mg per ml, especially 7 to 22 mg per ml. In a highly preferred embodiment 20 mg of glycine or alanine is employed per milliliter of reconstituted solution.

The amount of the alpha type interferon contained in the formulations of the present invention is $1 \times 10^4$ to $5 \times 10^8$ I.U., per milliliter of reconstituted solution. Preferably the amount of the alpha type interferon contained in the formulations of the present invention is $1 \times 10^6$ to $1 \times 10^8$ I.U. per milliliter of reconstituted solution. In other words, the ratio of glycine or alanine to the alpha type interferon in the formulations of the present invention will be about 5 to 150 milligrams of glycine or alanine for each $1 \times 10^4$ to $5 \times 10^8$ International Units of the alpha type interferon, preferably about 5 to 25 milligrams of glycine or alanine for each $1 \times 10^6$ to $1 \times 10^8$ International Units of alpha-interferon and most preferably 20 milligrams of glycine or alanine for each $1 \times 10^6$ to $1 \times 10^8$ International Units of alpha type interferon.

The specific activity of the alpha type interferon used in the formulations of the present invention should be at least $5 \times 10^7$ International Units/mg total protein, and preferably at least $1 \times 10^8$ International Units/mg total protein. Specific activity may be determined by measuring the antiviral activity as compared to the NIH reference standard and by measuring the total protein content using standard methods (e.g. the Lowry Method).

It will be understood that the water used in reconstituting the formulations of the present invention may also contain preservatives known to those skilled in the art, for example, thimerosal. These are advantageous where the solutions will be used for multiple dose applications rather than as a single dose, for example, nasal or ophthalmic solutions.

Human albumin is preferably added as a stabilizer to the formulations of the present invention in an amount up to about 10 milligrams of albumin per milliliter of reconstituted solution. If the amount of alpha type interferon in a milliliter of reconstituted solution is to be less than about $5 \times 10^6$ International Units, the addition of albumin is especially desirable.

In a preferred embodiment, the present invention relates to a lyophilized pharmaceutical composition, for reconstitution with water, comprising about $1 \times 10^4$ to $5 \times 10^8$ International Units of alpha-2 interferon, about 5 to 25 milligrams of glycine or alanine, a compatible buffer system that will maintain a pH of about 7.0 to 7.4, and about 1 milligram of albumin for each milliliter of water that will later be added during reconstitution.

In a highly preferred embodiment, the present invention relates to a lyophilized pharmaceutical composition, for reconstitution with water, comprising about $1 \times 10^6$ to $1 \times 10^8$ International Units of alpha-2 interferon, 20 mg of glycine or alanine, a compatible buffer system that will maintain a pH of about 7.0 to 7.4, and about 1 milligram of albumin for each milliliter of water that will later be added during reconstitution.

The following non-limiting examples illustrate the preparation of a sterile powder for preparing injectable solutions of alpha-1 and alpha-2 interferon:

EXAMPLE 1

| Solution for Lyophilization Formula (1 ml per vial) | (1000 vials) grams per liter |
|---|---|
| Alpha-2 Interferon | $7.5 \times 10^{10}$ I.U. |
| Sodium Phosphate, Dibasic, Anhydrous, Reagent | 2.27 |
| Sodium Monobasic Phosphate, USP | 0.55 |
| Glycine, USP | 20.0 |
| Albumin, Human, USP | 1.0 |
| Water for Injection, USP q.s. ad | 1.0 liter |

EXAMPLE 2

| Solution for Lyophilization Formula (1 ml per vial) | (1000 vials) grams per liter |
|---|---|
| Alpha-2 Interferon | $7.5 \times 10^{10}$ I.U. |
| Sodium Phosphate, Dibasic, Anhydrous, Reagent | 2.27 |
| Sodium Monobasic Phosphate, USP | 0.55 |
| Alanine | 20.0 |
| Albumin, Human, USP | 1.0 |
| Water for Injection, USP q.s. ad | 1.0 liter |

Method of Manufacture

1. Charge a portion of Water for Injection, USP to a suitable vessel equipped with an agitator.
2. Charge and dissolve with agitation Sodium Phosphate, Dibasic, Anhydrous, Reagent.
3. Charge and dissolve with agitation Monobasic Sodium Phosphate, USP.
4. Charge and dissolve with agitation Glycine, USP.
5. Charge and dissolve with agitation Albumin, Human, USP.
6. Charge and dissolve the Alpha-2 Interferon with agitation.
7. Bring the batch to final volume with Water for Injection, USP.
8. In a sterile area, aseptically filter the solution into a sterilized vessel through a sterilized 0.2 micron filter which has been washed and tested for integrity. Test the integrity of the filter after filtration.
9. Aseptically fill the solution into sterilized vials.
10. Aseptically load filled vial into a sterilized lyophilizer.
11. Aseptically lyophilize the solution.
12. Aseptically stopper the vials.
13. Apply seal and crimp the vials.

Method of Lyophilization (Using a Shelf Lyophilizer)

1. Precool the shelves to $-30°$ C.
2. Load the vials in the chamber.
3. Allow the solutions to freeze. Cool the condenser to $-45°$ C. or below. Start the vacuum.
4. Increase shelf temperatures at a relatively constant rate to $\pm 35°$ C. in 5 hours.
5. When the product temperature is at or above $+30°$ C. for 5 hours, flood the chamber with sterile nitrogen until it reaches atmospheric pressure. Stopper the vials in the chambers.
6. Remove the vials from the chamber and seal them.

EXAMPLE 3

Substituting alpha-1 interferon for alpha-2 interferon, similarly prepare lyophilized formulations of alpha-1 interferon.

I claim:

1. In a method for preparing a formulation of high specific activity alpha-type interferon having improved biological stability by lyophilizing a solution containing said alpha-type interferon to yield a reconstitutable lyophylizate, the improvement for further increasing said biological stability to a level such that the lyophilizate substantially retains its biological activity even when stored at 20° C. for at least six months which comprises: adding to said solution prior to lyophilization (a) a compatible buffer which will maintain the pH of the reconstituted solution within the range of about 6.5 to 8.0, and (b) glycine or alanine in an amount of 5 to 150 milligrams per milliliter of water to be added for reconstitution.

2. A method according to claim 1 wherein said solution to be lyophilized additionally contains up to 10 milligrams of human albumin for each milliliter of water that will be added during reconstitution.

3. A method according to claim 1 wherein the said alpha type interferon is alpha-2 interferon.

4. A method according to claim 1 wherein said compatible buffer maintains a pH at about 7.0 to 7.4 in the reconstituted solution.

5. A method according to claim 3 wherein about 5 to 25 mg of glycine is added for each $1 \times 10^4$ to $5 \times 10^8$ I.U. of the alpha-2 interferon mixture to be lyophilized.

6. A method according to claim 3 wherein about 5 to 25 mg of alanine is added for each $1 \times 10^4$ to $5 \times 10^8$ I.U. of the alpha-2 interferon mixture to be lyophilized.

7. A method according to claim 1 wherein the said alpha type interferon is alpha-1 interferon.

* * * * *